United States Patent
Babbush et al.

(10) Patent No.: US 11,763,187 B2
(45) Date of Patent: Sep. 19, 2023

(54) TRAINING QUANTUM EVOLUTIONS USING SUBLOGICAL CONTROLS

(71) Applicant: Google LLC, Mountain View, CA (US)

(72) Inventors: Ryan Babbush, Venice, CA (US); Hartmut Neven, Malibu, CA (US)

(73) Assignee: Google LLC, Mountain View, CA (US)

(*) Notice: Subject to any disclaimer, the term of this patent is extended or adjusted under 35 U.S.C. 154(b) by 0 days.

(21) Appl. No.: 18/147,144

(22) Filed: Dec. 28, 2022

(65) Prior Publication Data

US 2023/0134825 A1 May 4, 2023

Related U.S. Application Data (63) Continuation of application No. 17/339,125, filed on Jun. 4, 2021, now Pat. No. 11,562,285, which is a continuation of application No. 16/355,293, filed on Mar. 15, 2019, now Pat. No. 11,055,626, which is a
(Continued)

(51) Int. Cl.
| | |
|---|---|
| G06N 10/00 | (2022.01) |
| G06N 20/00 | (2019.01) |
| G06F 15/16 | (2006.01) |
| B82Y 10/00 | (2011.01) |

(52) U.S. Cl.
CPC .......... *G06N 10/00* (2019.01); *G06F 15/16* (2013.01); *G06N 20/00* (2019.01); *B82Y 10/00* (2013.01)

(58) Field of Classification Search
None
See application file for complete search history.

(56) References Cited

U.S. PATENT DOCUMENTS

| | | |
|---|---|---|
| 2011/0060710 A1 | 3/2011 | Amin |
| 2012/0319085 A1 | 12/2012 | Gambetta et al. |
| 2015/0032994 A1 | 1/2015 | Chudak et al. |

(Continued)

FOREIGN PATENT DOCUMENTS

| | | |
|---|---|---|
| CN | 203872190 | 10/2014 |
| CN | 104572589 | 4/2015 |

(Continued)

OTHER PUBLICATIONS

Babbush et al., "Construction of non-convex polynomial loss functions for training a binary classifier with quantum annealing," arXiv, Jun. 2014, 15 pages.
(Continued)

*Primary Examiner* — Whitney Moore
(74) *Attorney, Agent, or Firm* — Fish & Richardson P.C.

(57) ABSTRACT

Methods, systems, and apparatus for training quantum evolutions using sub-logical controls. In one aspect, a method includes the actions of accessing quantum hardware, wherein the quantum hardware includes a quantum system comprising one or more multi-level quantum subsystems; one or more control devices that operate on the one or more multi-level quantum subsystems according to one or more respective control parameters that relate to a parameter of a physical environment in which the multi-level quantum subsystems are located; initializing the quantum system in an initial quantum state, wherein an initial set of control parameters form a parameterization that defines the initial quantum state; obtaining one or more quantum system observables and one or more target quantum states; and iteratively training until an occurrence of a completion event.

20 Claims, 3 Drawing Sheets

Related U.S. Application Data continuation of application No. 15/171,778, filed on Jun. 2, 2016, now Pat. No. 10,275,717.

(56) References Cited

U.S. PATENT DOCUMENTS

| | | |
|---|---|---|
| 2016/0071021 A1 | 3/2016 | Raymond |
| 2019/0266510 A1 | 8/2019 | Yarkoni et al. |
| 2020/0005186 A1 | 1/2020 | Romero et al. |

FOREIGN PATENT DOCUMENTS

| | | |
|---|---|---|
| CN | 105531725 | 4/2016 |
| JP | 2013-114366 | 6/2013 |
| WO | WO 2013006836 | 1/2013 |

OTHER PUBLICATIONS

Behrman et al. "Quantum algorithm design learning using dynamic learning," arXiv, Aug. 11, 2008, 18 pages.
CA Office Action in Canadian Appln. No. 3,026,443, dated Sep. 9, 2020, 3 pages.
CA Office Action in Canadian Appln. No. 3026443, dated Oct. 10, 2019, 5 pages.
Caneva et al., "Chopped random-basis quantum optimization," Physical Review A 84, 022326, Aug. 2011, 10 pages.
Extended European Search Report in European Appln. No. 21213547.9, dated Apr. 25, 2022, 13 pages.
International Preliminary Report on Patentability in International Appln. No. PCT/uS2016/067471, dated Sep. 5, 2018, 18 pages.
International Search Report and Written Opinion in International Appln. No. PCT/US2016/067471, dated Mar. 29, 2017, 16 pages.
International Written Opinion in International Appln. No. PCT/US2016/067471, dated Apr. 30, 2018, 7 pages.
Leghtas et al., "Confining the state of light to a quantum manifold by engineered two-photon loss," Science, Feb. 20, 2015, 347(6224):853-857.
McClean et al., "Exploiting Locality in Quantum Computation for Quantum Chemistry," The Journal of Physical Chemistry Letters, Nov. 2014: 5(24):4368-4380.
McClean et al., "The theory of variational hybrid quantum-classical algorithms," arXiv, Sep. 14, 2015, 20 pages.
Notice of Reasons for Rejection in Japanese Appln. No. 2018-562952, dated Jan. 23, 2020, 8 pages (with English translation).
O'Malley et al., "Scalable quantum simulation of molecular energies," Physical Review X, Jul. 2016, 6(3):1-12.
Office Action in Australian Appln. No. 2019283 845, dated Sep. 2, 2020, 5 pages.
Office Action in Australian Appln. No. 2021203 607, dated May 23, 2022, 2 pages.
Office Action in Chinese Appln. No. 201680087746.8, dated Jul. 5, 2021, 12 pages (with English translation).
Office Action in European Appln. No. 16825955, dated Apr. 2, 2020, 7 pages.
Office Action in European Appln. No. 16825955, dated Feb. 4, 2020, 7 pages.
Office Action in European Appln. No. 16825955.4, dated Jun. 8, 2021, 8 pages.
Office Action in European Appln. No. 16825955.4, dated Nov. 24, 2020, 8 pages.
Peruzzo et al., "A variational eigenvalue solver on a photonic quantum processor," Nature Communications 5:4213, Jul. 2014, 1-7.
Shen et al., "Quantum Implementation of Unitary Coupled Cluster for Simulating Molecular Electronic Structure," arXiv, Jun. 2015, 1-24.
Wecker et al., "Towards Practical Quantum Variational Algorithms," Physical Review A 92, 042303, Sep. 2015, 11 pages.
Wiebe et al., "Quantum Deep Learning," arXiv: 1412.3489, Dec. 2014, 34 pages.
Yung et al., "From transistor to trapped-ion computers for quantum chemistry," Scientific Reports 4:3589, Jan. 2014, 1-7.

TRAINING QUANTUM EVOLUTIONS USING SUBLOGICAL CONTROLS

CROSS-REFERENCE TO RELATED APPLICATIONS

This application is a continuation application of, and claims priority to, U.S. patent application Ser. No. 17/339,125, titled "TRAINING QUANTUM EVOLUTIONS USING SUBLOGICAL CONTROLS," filed on Jun. 4, 2021, which is a continuation application of, and claims priority to, U.S. patent application Ser. No. 16/355,293, now U.S. Pat. No. 11,055,626, titled "TRAINING QUANTUM EVOLUTIONS USING SUBLOGICAL CONTROLS," filed on Mar. 15, 2019, which is a continuation application of, and claims priority to, U.S. patent application Ser. No. 15/171,778, now U.S. Pat. No. 10,275,717, titled "TRAINING QUANTUM EVOLUTIONS USING SUBLOGICAL CONTROLS," filed on Jun. 2, 2016. The disclosures of the foregoing applications are incorporated herein by reference in their entirety for all purposes.

BACKGROUND

This specification relates to quantum computing.

Quantum variational eigensolvers have been proposed as a method to prepare and study the states of physically interesting systems. Digital implementations of quantum variational eigensolvers use quantum logic gates that execute precisely known operations on qubits.

SUMMARY

This specification describes technologies for training quantum evolutions of an initial quantum state to realize a target quantum state with defined target characteristics. The quantum evolutions of the initial quantum state are trained using adjustable analogue evolutions defined through the tuning of fundamental hardware elements, such as control knobs that may typically be used to calibrate individual quantum gates.

In general, one innovative aspect of the subject matter described in this specification can be implemented in a method that includes accessing quantum hardware, wherein the quantum hardware comprises a quantum system comprising one or more multi-level quantum subsystems; one or more control devices that operate on the one or more multi-level quantum subsystems according to one or more respective control parameters that relate to a parameter of a physical environment in which the multi-level quantum subsystems are located; initializing the quantum system in an initial quantum state, wherein an initial set of control parameters form a parameterization that defines the initial quantum state; obtaining one or more quantum system observables and one or more target quantum states; and iteratively training until an occurrence of a completion event.

Other implementations of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations iteratively training comprises iteratively training changes from the initial quantum state to achieve the one or more target quantum states.

In further implementations iteratively training comprises iteratively training, until the occurrence of a completion event, evolutions of the initial quantum state and subsequent quantum states to realize the one or more target quantum states.

In some cases the evolutions are analog evolutions.

In some implementations iteratively training comprises, for each iteration: determining a value of a cost function that is based on a current quantum state for the iteration and the one or more of the quantum system observables; minimizing the value of the cost function to determine updated values of the control parameters that define the current quantum state; and determining whether the completion event has occurred.

In other implementations minimizing the value of the cost function to determine updated values of the control parameters comprises adjusting the control parameters.

In some cases the method further comprises, in response to determining that the completion event has occurred, providing the one or more target quantum states for experimental probing.

In some implementations (i) at least one of the quantum system observables comprises a Hamiltonian of the quantum system, (ii) the one or more target quantum states comprise one or more eigenstates of the Hamiltonian, and (iii) experimental probing comprises measuring the energy of one or more of the eigenstates to determine corresponding energy eigenvalues of the eigenstates.

In other implementations (i) the system observable is a molecular electronic structure Hamiltonian, (ii) the one or more target quantum states comprise a ground state of the molecular electronic structure Hamiltonian, and (iii) experimental probing comprises measuring the target quantum state to determine the ground state energy.

In some cases the value of the cost function that is based on the quantum state and one or more of the system observables is an expectation value of the quantum state and one or more of the system observables.

In other cases determining an expectation value of the quantum state and one or more of the system observables comprises: repeatedly initializing the quantum system in an initial quantum state; for each initialized quantum state, measuring the one or more system observables to determine a set of measurement results; based on the set of measurement results, determining an expectation value of the quantum state and one or more of the system observables.

In some cases each initialized quantum state is different from each other initialized quantum state.

In some implementations determining an expectation value of the quantum state and one or more of the system observables comprises determining an expectation value of a density operator and the one or more system observables.

In other implementations obtaining one or more target quantum states comprises encoding a solution to an optimization problem into the ground state of the quantum system.

In some cases the method further comprises obtaining a solution to the optimization problem from the experimental probing.

In some implementations (i) the initial quantum state encodes training data, (ii) the one or more system observables serve as a prediction function, and (iii) iteratively training changes from the initial quantum state comprises solving a machine learning problem.

In some cases the quantum hardware comprises a quantum circuit.

In some cases the control devices include one or more quantum gates that operate on the quantum system through one or more respective control parameters.

In some implementations the method further comprises calibrating one or more of the quantum gates, comprising, for each quantum gate that is to be calibrated: defining a correct action of the quantum gate on the quantum system; performing a measurement to determine the action of the quantum gate on the quantum system; and in response to determining that the action of the quantum gate on the quantum system is not correct, adjusting the corresponding control parameters for the quantum gate.

In some cases iteratively training comprises combining iterative training with calibrating one or more of the quantum gates.

In other cases minimizing the value of the cost function to determine updated values of the control parameters comprises performing a gradient-free greedy minimization method.

In some implementations the completion event is that the determined value of the cost function that is based on the quantum state and one or more of the system observables converges.

In some cases the initial quantum state is a state of a resonator that is coupled to a superconducting qubit.

The subject matter described in this specification can be implemented in particular ways so as to realize one or more of the following advantages.

A system training quantum evolutions using sublogical controls parameterizes quantum evolution using the natural control parameters of a quantum system by performing variational minimization procedures by directly adjusting control parameters of control devices included in the system, e.g., by adjusting a voltage on a digital to analog converter. By exploiting low level control to parameterize an ansatz, a system training quantum evolutions using sublogical controls is able to eschew precise knowledge of an effective circuit in exchange for an overall mapping that is agnostic to systematic errors and robust to many control and calibration problems, as opposed to systems that train quantum evolutions using adjustable quantum gates. Furthermore, using low level controls may allow for a fundamentally more accurate representation of a desired state, since an increase in control over the evolution of the state is achieved. Using hardware level controls provides the highest amount of control over the evolution and state that is prepared, therefore, even in the presence of errors, a more precise ansatz is created for the model that is being simulated.

A system training quantum evolutions using sublogical controls adaptively trains quantum evolutions to realize target quantum states with target characteristics without using a parameterized digital quantum circuit, thus reducing the experimental complexity of the system since such quantum circuits may be very complicated to implement. Rather, a system training quantum evolutions using sublogical controls may abandon the concept of digital quantum gates in favour of adjustable analog evolutions defined using control parameters typically reserved for the calibration of individual gates, unlike other quantum evolution training systems. By operating at the level of fundamental hardware elements, a system training quantum evolutions using sublogical controls does not require precise knowledge of an effective circuit and rather performs an overall mapping that is agnostic to systematic errors and robust to many control and calibration problems.

Digital quantum circuits may consist of quantum logic gates that execute precise operations on qubits, or in some examples qudits. In many settings quantum logic gate model algorithms specify a quantum circuit and require an experimentalist to execute the specified quantum circuit with minimal error. This may be a challenging task, since the implementation of a quantum logic gate model algorithm may require many quantum logic gates. Scalable computations based on the quantum logic gate model may therefore require costly processes, such as quantum error correction. Furthermore, each gate in the circuit must be calibrated prior to execution. Systems that do not train quantum evolutions using sublogical controls may calibrate quantum gates by carefully adjusting hardware control parameters and performing a classical minimization loop to perfect each individual gate. Thus, a great amount of effort may be required in order to apply a quantum circuit, which in any case will not be error free. In fact, the system may be subject to a large amount of errors, such as control errors where the error is caused by pulses not perfectly forming the gate, as is often the case, or errors resulting from noise coupling with the system.

A system training quantum evolutions using sublogical controls may be applicable in a variety of settings and used to manipulate various types of controllable states, such as those that live in resonators that are attached to superconducting qubits. Such resonator states are controllable and define an appropriate variational ansatz.

A system training quantum evolutions using sublogical controls may be used instead of or in conjunction with standard methods for gate calibration in order to improve system scalability and performance. Quantum gates may be generated by precise evolutions of a quantum system under particular Hamiltonians. For example, in the case of superconducting Gmon qubits, the system may be described by the Hamiltonian given by equation (1) below.

$$H = \sum_{i=1}^{N} a_i(t)X_i + \sum_{i=1}^{N} b_i(t)Y_i + \sum_{i=1}^{N} c_i(t)Z_i + \sum_{\langle ij \rangle} g_{ij}(t)\frac{X_iX_j + Y_iY_j}{2} \quad (1)$$

$$H = \sum_{i=1}^{N} a_i(t)X_i + \sum_{i=1}^{N} b_i(t)Y_i + \sum_{i=1}^{N} c_i(t)Z_i + \sum_{\langle ij \rangle} g_{ij}(t)\frac{X_iX_j + Y_iY_j}{2} \quad (1)$$

In equation (1), $X_i$, $Y_i$, $Z_i$ are Pauli operators and $a_i(t)$, $b_i(t)$, $c_i(t)$ and $g_{ij}(t)$ are time-dependent profiles generated by microwave pulses that are sent through wires in the hardware. In order to execute a quantum circuit an experimentalist may be required to first calibrate all the quantum gates included in the quantum circuit by sending specific pulses through the wires in the hardware. In the case of superconducting electronics, the pulses may be thought of as being formed from a Fourier series—for example, a pulse which induces a local Y field on a qubit q may be given by $b_q(t) = \sum_{\kappa=1}^{K} A_\kappa \sin(\kappa\omega_0 t) + B_\kappa \cos \kappa\omega_0 t$ where $\omega_0$ is a fundamental frequency and $A_\kappa$, $B_\kappa$ determine the pulse shape. At the hardware level, the pulses $Y_1$ and $Y_2$ may be engineered using a digital to analog converter (DAC) which sets the voltage versus time for each line.

It may be possible to determine precisely or approximately which pulses are needed in order to perform desired quantum gates, and then Fourier transform the determined pulses and program the pulses into appropriate DACs. However, the exact mapping between settings of a DAC and the actual pulses seen by the system on which the pulses act is not precise for real experimental systems in a laboratory. For example, a DAC may be programmed a particular way in order to perform a particular tasks, however, in practice, the physical action of the DAC may deviate from the intended action, e.g., due to unknown persistent systematic errors. For example, a DAC in a laboratory may be at room temperature whereas a quantum chip may be at milikelvin temperatures, leading to unpredictable or unwanted transformations as the signal travels down to the chip due to a changing temperature of the waveguide.

Unlike other systems, a system training quantum evolutions using sublogical controls may not require protocols from quantum control theory, such as a chopped random basis scheme, in order to form clean quantum gates. Similarly, unlike other systems which implement quantum control procedures to tune individual gates, as described above a system training quantum evolutions using sublogical controls may be used to calibrate or train an entire circuit. In some implementations, e.g., for systems with advanced architectures, it may further be advantageous to combine the training of quantum evolutions using sublogical controls with the standard methods for gate calibration described above.

Furthermore, a system training quantum evolutions using sublogical controls may be more robust and avoid introducing certain control or systematic errors into the quantum system compared to systems that do not train quantum evolutions using sublogical controls. For example, experimentalists may typically form gates out of sublogical controls using control theory feedback since the action of the control parameters on the system may not be entirely known or predictable. However, such control or systematic errors are not problematic for a system training quantum evolutions using sublogical controls since the classical minimization process used to determine a control parameter update is agnostic to exactly what is happening in the hardware—it is not problematic if it is assumed that the ansatz is parameterized in a certain way but it is actually parameterized slightly differently if the parameterization does not change.

In addition, a system training quantum evolutions using sublogical controls is able to tolerate leakage away from qubit states, which is most quantum computing settings is extremely problematic. Defining a variational ansatz on a qubit manifold but permitting the state or parts of the state to leave the manifold is permissible, equivalent to performing a non-unitary operation and renormalizing the state.

Unlike other quantum evolution training systems, a system training quantum evolutions using sublogical controls may be applied to multi-level quantum systems, e.g., multi-level systems other than qubits, since any parameterized quantum evolution of any quantum system may be used to define an ansatz. Therefore, the practicality and applicability of systems training quantum evolutions using sublogical controls is greatly improved since quantum hardware often suffers from qubit leakage, i.e., qubits may only be approximately qubits and may at times occupy higher energy levels. In addition, a system training quantum evolutions using sublogical controls may be applied to train quantum evolutions and realize quantum states with target characteristics even in the presence of noise, i.e., the system training quantum evolutions using sublogical controls does not require that the evolution is closed.

Training quantum evolutions using sublogical controls may be applied to a variety of settings, in particular settings of industrial value. Generally, any physical system that is hard to study due to quantum mechanics may benefit from implementing a system for training quantum evolutions using sublogical controls. For example, training quantum evolutions using sublogical controls may be used to prepare the ground states of the molecular electronic structure Hamiltonian that describes the energetics of molecules—a compelling industrial application of a small quantum computer. Solving such problems on a quantum computer would provide energy surfaces that describe chemical reactions and may be used to predict chemical rates, thus dramatically accelerating, for example, drug discovery, solar cell design and industrial catalyst development. As another example, training quantum evolutions using sublogical controls may be used to study the properties of high temperature superconductors, e.g., by studying the Fermi-Hubbard model. As a further example, training quantum evolutions using sublogical controls may be used to simulate models from condensed matter physics, e.g., for the purpose of investigating and designing material properties.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes an apparatus and method for adaptively training quantum evolutions to realize quantum states with target characteristics using hardware level control. The apparatus and method have applications in a variety of settings, including machine learning tasks and quantum simulation e.g., the preparation and study of physically interesting states.

For example, it may be required to prepare or solve for a quantum state $|\psi\rangle$ of a quantum system which is a lowest energy eigenstate of a Hamiltonian H so that $H|\psi\rangle = E_0|\psi\rangle$. One method for approximately preparing $|\psi\rangle$ is to parameterize a guess wavefunction $|\phi(\vec{\theta})\rangle$, known as an ansatz, in terms of a polynomial number of parameters denoted by the vector $\vec{\theta}$. The quantum variational principle then holds that $$\frac{\langle \phi(\vec{\theta})|H|\phi(\vec{\theta})\rangle}{\langle \phi(\vec{\theta})|\phi(\vec{\theta})\rangle} \geq E_0,$$

$$\frac{\langle \phi(\vec{\theta})|H|\phi(\vec{\theta})\rangle}{\langle \phi(\vec{\theta})|\phi(\vec{\theta})\rangle} \geq E_0,$$

$|\phi(\vec{\theta})\rangle |\psi\rangle |\psi\rangle |\phi(\vec{\theta})\rangle \vec{\theta} |\phi(\vec{\theta})\rangle$ with equality when =. Accordingly, may be approximated with by solving for which makes the above inequality as tight as possible within the parameterization. This specification describes an apparatus and method for parameterizing using a low level, i.e., sublogical, control that is based on the natural control knobs of the corresponding quantum system to parameterize an ansatz.

$$|\phi(\vec{\theta})\rangle |\psi\rangle |\psi\rangle |\phi(\vec{\theta})\rangle \vec{\theta} |\phi(\vec{\theta})\rangle$$

Example Operating Environment

Figure 1:
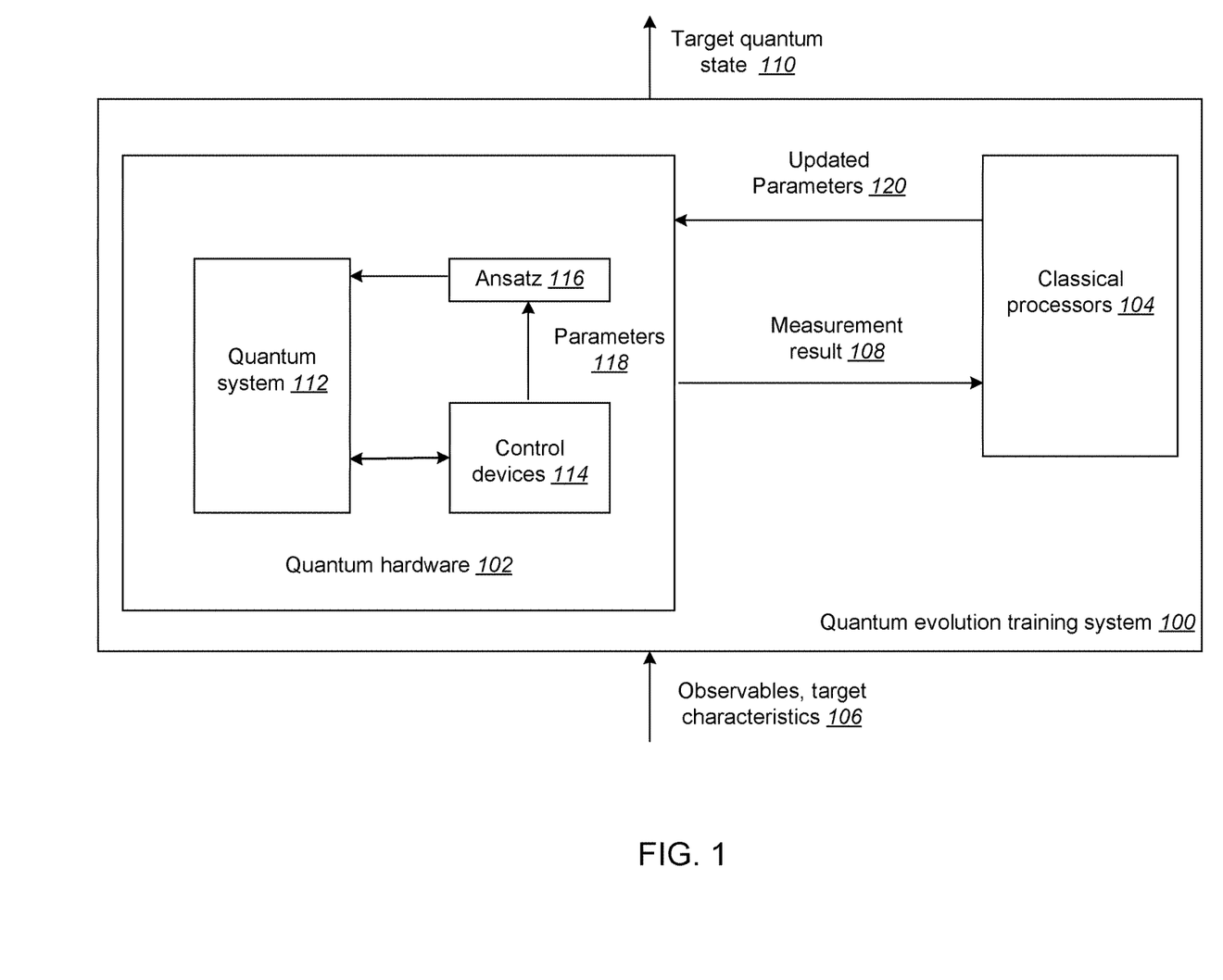
FIG. 1 depicts an example quantum evolution training system.

FIG. 1 depicts an example quantum evolution training system 100. The example system 100 is an example of a system implemented as classical or quantum computer programs on one or more classical computers or quantum computing devices in one or more locations, in which the systems, components, and techniques described below can be implemented.

The quantum evolution training system 100 may include quantum hardware 102 in data communication with a classical processor 104. The quantum evolution training system 100 may receive as input data that may include data specifying one or more quantum system observables and one or more target quantum states, for example quantum states with corresponding target characteristics, e.g., observables and target characteristics 106. The evolution training system 100 may generate as output data specifying one or more target quantum states, e.g., target quantum state 110.

The one or more quantum system observables may include measureable operators, e.g., a Hamiltonian operator, momentum operator or position operator. The target quantum states may include one or more eigenstates of a Hamiltonian operator, e.g., a ground state of a Hamiltonian operator. In some implementations a solution to an optimization problem may be encoded into the ground state of a Hamiltonian operator. The data specifying target quantum state 110 may be further provided for experimental probing or post processing, e.g., the energy of the target quantum state may be measured to determine a corresponding energy eigenvalue.

The quantum hardware 102 may include a quantum system 112, control devices 114 and data specifying an ansatz 116. The quantum system 112 may include one or more multi-level quantum subsystems, e.g., qubits or qudits. In some implementations the multi-level quantum subsystems may be superconducting qubits, e.g., Gmon qubits. The type of multi-level quantum subsystems that the system 100 utilizes is dependent on the application in which the system 100 is applied to. For example, in some cases it may be convenient to include one or more resonators attached to one or more superconducting qubits, e.g., Gmon or Xmon qubits. In other cases ion traps, photonic devices or superconducting cavities (with which states may be prepared without requiring qubits) may be used. Further examples of realizations of multi-level quantum subsystems include fluxmon qubits, silicon quantum dots or phosphorus impurity qubits.

The one or more control devices 114 may be configured to operate on the multi-level quantum subsystems 112 through one or more respective control parameters 118, e.g., one or more physical control parameters. For example, in some implementations the multi-level quantum subsystems may be superconducting qubits and the control devices 114 may include one or more digital to analog converter (DACs) with respective voltage physical control parameters. In other implementations the quantum system 112 may include a quantum circuit and the control devices 114 may include one or more quantum logic gates that operate on the quantum system 112 through microwave pulse physical control parameters that are sent through wires included in the quantum hardware 102. Further examples of control devices include arbitrary waveform generators, which may create signals that a DAC controls. The control parameters may include qubit frequencies.

The data specifying an ansatz 116 includes a set of parameters 118 and is chosen based on knowledge of the quantum system 112 and the control devices 114 that act on the quantum system 112. For example, the ansatz 116 may be a variational ansatz that uses information about the quantum hardware 102, such as the control devices 114 and their respective control parameters 118, to determine a parameterization for the state of the quantum system 112. In some implementations the quantum hardware 102 is directly used to parameterize the ansatz 116 that is the variational class of parameters that form the variational ansatz 116 may include the sublogical, physical control parameters of the control devices 114.

The quantum hardware 102 may be configured to perform quantum measurements on the quantum system 112 and send measurement results to the classical processors 104. In addition, the quantum hardware 102 may be configured to receive data specifying updated physical control parameter values 120 from the classical processors 104. The quantum hardware 102 may use the received updated values of physical control parameter values 120 to update the action of the control devices 114 on the quantum system 112, thus training the evolution of the quantum state 112. For example, the quantum hardware may receive data specifying new values representing voltage strengths of one or more DACs included in the control devices 114 and may update the action of the DACs on the quantum system 112 accordingly.

The classical processors 104 may be configured to initialize the quantum system 112 in an initial quantum state, e.g., by sending data to the quantum hardware 102 specifying an initial set of parameters, and to iteratively train analog evolutions of the initial quantum state and subsequent quantum states to realize the target quantum state 100 with the target characteristics 106. The classical processors may be configured to iteratively train analog evolutions of the initial quantum state until the occurrence of a completion event, e.g., until received measurement results 108 converge. The classical processors 104 may determine that a completion event has occurred and provide the target quantum state 110 with defined target characteristics 106 for experimental probing, as described above.

The classical processors 104 may further be configured to determine a value of a cost function that is based on a quantum state of the quantum system 112 and one or more of the system observables 106 and to minimize the value of the cost function to determine updated values of the physical control parameters 120. For example, the classical processors may be configured to perform minimization methods such as gradient-free minimization methods including Powell's method or Nelder-Mead.

In some implementations the value of the cost function that is based on the quantum state of the quantum system 112 and one or more of the system observables 106 is an expectation value of the quantum state and the system observables. For example, the classical processors 104 may be configured to repeatedly initialize the quantum system in an initial quantum state and for each initialized quantum state, initiate measurements of one or more of the system observables to determine a set of measurement results, e.g., a set of measurement results 108. Based upon the set of measurement results, the classical processors 104 may be configured to determine a corresponding expectation value of the quantum state and one or more of the system observables. In other examples the classical processors 104 may be configured to determine an expectation value of a density operator and the one or more system observables.

The classical processors 104 may be further configured to calibrate one or more quantum gates that may be included in the quantum hardware 102. For example, the classical processors may be configured to define a correct action of a quantum gate on the quantum system 112, perform or initiate a measurement of the quantum system 112 to determine the action of the quantum gate on the quantum system 112 and in response to determining that the action of the quantum gate on the quantum system is not correct, adjust the corresponding physical control parameters for the quantum gate and provide the adjusted updated physical control parameters 120 to the quantum hardware 102. In some implementations the classical processor may be configured to iteratively train analog evolutions of the a quantum state to realize a target quantum state with target characteristics by combining iterative training of analog evolutions of the initial quantum state and subsequent quantum states with gate calibration techniques.

Programming the Hardware

Figure 2:
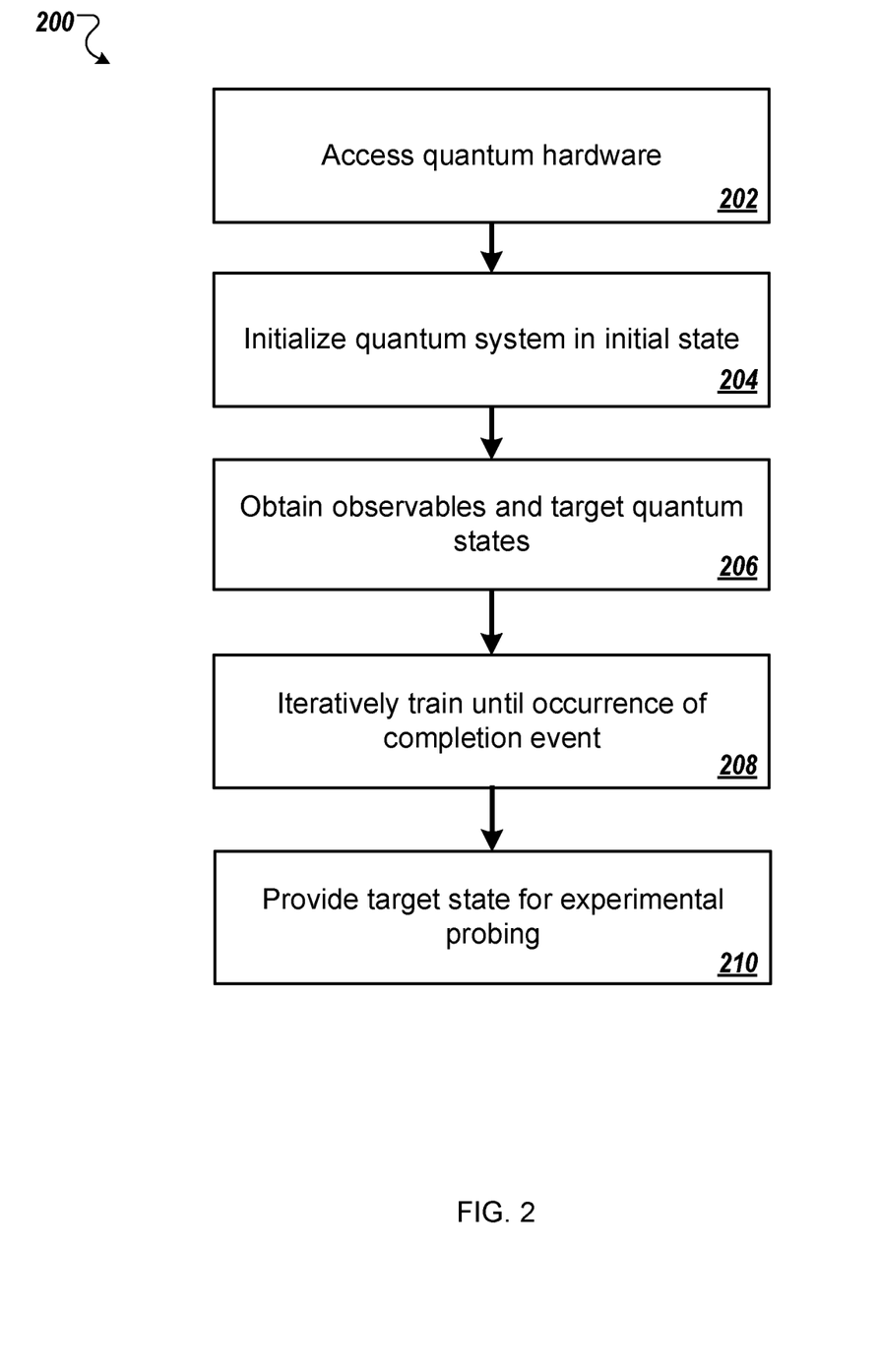
FIG. 2 is a flow diagram of an example process for training quantum evolutions using sublogical controls.

FIG. 2 is a flowchart of an example process 200 for training quantum evolutions using sublogical controls. For convenience, the process 200 will be described as being performed by a system of one or more classical or quantum computing devices located in one or more locations. For example, a quantum evolution training system, e.g., the quantum evolution training system 100 of FIG. 1, appropriately programmed in accordance with this specification, can perform the process 200.

The system accesses quantum hardware, e.g., quantum hardware 102 of FIG. 1 (step 202). The quantum hardware may include a quantum system comprising one or more multi-level quantum subsystems, e.g., quantum system 112 of FIG. 1, and one or more control devices that operate on the one or more multi-level quantum subsystems according to one or more respective control parameters, e.g., control devices 114 and respective control parameters 118 of FIG. 1. The respective control parameters may include physical control parameters. Example multi-level quantum systems and control devices that operate thereon are described above with reference to FIG. 1.

The quantum hardware may include a quantum circuit which, in turn, may include one or more quantum logic gates that operate on the quantum system through one or more respective control parameters. In some implementations the system may calibrate one or more of the quantum logic gates included in the quantum hardware using the control devices. For example, for each quantum gate that is to be calibrated, the system may define a correct action of the quantum gate on the quantum system and perform a measurement to determine the action of the quantum gate on the quantum system. In response to determining that the action of the quantum gate on the quantum system is not correct, the system may adjust the corresponding control parameters for the quantum gate. In some implementations the system may combine the process 200 with quantum gate calibration techniques, e.g., when the quantum hardware includes advanced architecture.

The system initializes the quantum system in an initial quantum state (step 204). An initial set of control parameters may form a parameterization that defines the initial quantum state. The initialized quantum state may be a parameterized quantum state, e.g., an ansatz, or "guess", wavefunction with the control parameters forming the parameterization for the quantum state. In some implementations the initial quantum state is a state of a resonator that is coupled to a superconducting qubit. Such resonator states are controllable and may form a variational ansatz.

The system obtains one or more quantum system observables and one or more target quantum states (step 206).

In some implementations the process 200 for training quantum evolutions using sublogical controls may be applied to quantum simulation tasks, e.g., preparing and studying physically interesting states. In such cases, the system may receive one or more quantum system observables that include a Hamiltonian of the quantum system. The system may further receive one or more target quantum states that include one or more eigenstates of the defined Hamiltonian. For example, the received quantum system observable may be a molecular electronic structure Hamiltonian and a corresponding target quantum state may include a ground state of the molecular electronic structure Hamiltonian. In another example, the received quantum system observable may be a Fermi-Hubbard model Hamiltonian and corresponding target quantum states may include one or more eigenstates of the Hamiltonian. Generally, the process 200 may be applied to quantum simulation tasks that involve the study of any physical system that is hard to study due to quantum mechanics.

In other implementations the process for training quantum evolutions using sublogical controls 200 may be applied to machine learning tasks, e.g., solving optimization tasks. In such cases, the system may receive one or more quantum system observables that may include a Hamiltonian of the quantum system. The system may further receive a target quantum state that encodes a solution to an optimization task into the ground state of the quantum system. Applications of training quantum evolutions using sublogical controls to machine learning tasks is described in more detail below with reference to FIG. 3.

The system iteratively trains until the occurrence of a completion event (step 208). The system may iteratively train changes from the initial quantum state to achieve the one or more target states. In some implementations the system may iteratively train evolutions of the initial quantum state and subsequent quantum states to realize the one or more target quantum states. The evolutions may be analog evolutions. The iterative training may be performed until the occurrence of a completion event, e.g., until the analog evolutions of the initial quantum state and subsequent quantum states converge. Iteratively training analog evolutions of a quantum state is described in more detail below with reference to FIG. 3.

The system provides the target quantum state for experimental probing (step 210). The system may provide the target quantum state for experimental probing in response to determining that the completion event has occurred. For example, as described above with reference to step 206, in some implementations the process 200 may be applied to quantum simulation tasks, e.g., preparing and studying physically interesting states. In examples where at least one of the system observables includes a Hamiltonian of the quantum system and the one or more target quantum states include one or more eigenstates of the Hamiltonian, experimental probing may include measuring the energy of one or more of the eigenstates to determine corresponding energy eigenvalues of the eigenstates. For example, in implementations where a system observable is a molecular electronic structure Hamiltonian and a target quantum state includes a ground state of the molecular electronic structure Hamiltonian, experimental probing may include measuring the target quantum state to determine the ground state energy.

Similarly, as described above with reference to step 206, in other implementations the process 200 may be applied to machine learning tasks, e.g., solving optimization tasks. In examples where target characteristics of the target quantum state include encoding a solution to an optimization task into the ground state of the quantum system, experimental probing may include solving a machine learning problem, e.g., obtaining a solution to the optimization problem.

Figure 3:
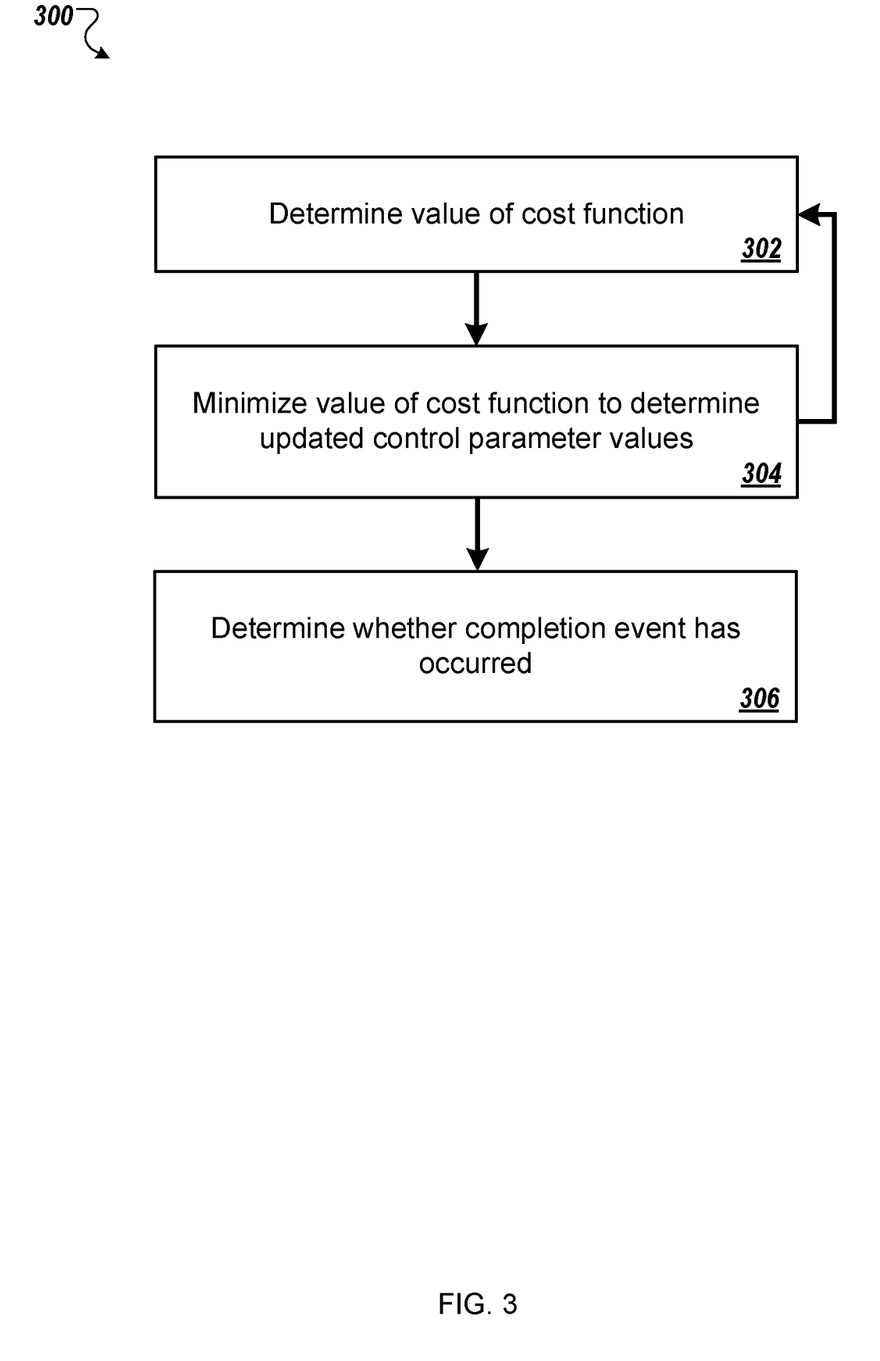
FIG. 3 is a flow diagram of an example iteration for training quantum evolutions of a quantum state.

FIG. 3 is a flowchart of an example process 300 for training analog evolutions of a quantum state. For example, the process 300 may describe an iteration of training evolutions of an initial quantum state and subsequent quantum states to realize a target quantum state, as described above at step 208 of FIG. 2. For convenience, the process 300 will be described as being performed by one or more computing devices located in one or more locations. For example, a quantum evolution training system, e.g., the quantum evolution training system 100 of FIG. 1, appropriately programmed in accordance with this specification, can perform the process 300.

The quantum evolution training system determines a value of a cost function (step 302). The cost function may be based on a quantum state for the iteration and one or more system observables.

In some implementations the value of the cost function that is based on a quantum state and one or more system observables may be an expectation value of the quantum state and one or more of the system observables. The quantum evolution training system may determine an expectation value of the quantum state and one or more of the system observables by repeatedly initializing the quantum system in an initial quantum state. In some implementations each initialized quantum state is different from each other initialized quantum state. For each initialized quantum state, the system may measure the one or more system observables to determine a set of measurement results. Based on the set of measurement results, the quantum evolution training system may determine an expectation value of the quantum state and one or more of the system observables. In some implementations the quantum evolution training system may determine an expectation value of the quantum state and one or more of the system observables by determining an expectation value of a density operator and the one or more system observables.

In some implementations the value of the cost function that is based on a quantum state and one or more system observables may not be an expectation value of the quantum state and a system Hamiltonian but rather a minimum value of an objective function defined by another observable of the quantum system. For example, as described above with reference to FIG. 2, the processes 200 and 300 may be applied to machine learning tasks, e.g., solving optimization tasks, which may always be expressed as a task that requires the minimization of a corresponding objective function.

An example of such a machine learning task is the training of a binary classifier using noisy data. This may be viewed as a machine learning problem in which training data is provided as a vector of N features denoted by $x_i$. There may be M training examples that may be each associated with a binary label, e.g., 0 or 1, denoted as $y_i$. The training problem may be formulated as to determine an optimal classifier that predicts the data by classifying example i. Therefore, the goal may be to find a function F such that $F(x_i)=y_i$ for all $(x_i, y_i)$ in the training set. This problem may become formally hard when there is label noise in the data which may make it impossible to satisfy all examples. In order to train classifiers with noisy data non-convex loss functions may be used as 0-1 loss, which are robust to label noise. For example, if F is parameterized in terms of variables $\vec{\theta}$ the training problem may be formulated as to choose $\vec{\theta}$ in a way that minimizes the quantity $E(\vec{\theta})=\Sigma_{i=1}^{M} \text{sign}(y_i F(x_i))$. The classifier may be viewed as a hyperplane in feature space which divides data points into negative and positive classifications. The distance that example i falls from the classification hyperplane may be referred to as a margin. In this example, the sign function is a loss function and $y_i F(x_i)$ is a margin. A negative margin may represent a classification opposite the training label and a positive margin may represent a classification consistent with the training label.

This optimization may be performed using quantum evolutions that are trained with sublogical controls, e.g., using processes 200 and 300. For example, at step 204 of process 200 the corresponding quantum hardware may be initialized in a state that encodes one of the $x_i$, denoted for example by $|\phi_i\rangle$, and F may be defined as an observable of the output state $U(\vec{\theta})|\phi_i\rangle$, where $U(\vec{\theta})$ is the training objective which may be computed by using the quantum circuit to classify each of the $x_i$. The value of the cost function that is to be minimized may therefore be given by $\langle\phi_i|U^{\dagger}(\vec{\theta}) FU(\vec{\theta})|\phi_i\rangle$. The margin, loss and empirical risk may then be computed using standard techniques. Once a cost function is defined, a process for training quantum evolutions using sublogical controls may be used to find a quantum state which minimizes the defined cost function.

An additional example of a machine learning task to which the processes 200 and 300 may be applied is the training of a neural network. The training of a neural network may be cast as a process for training quantum evolutions using sublogical controls by choosing, for example, a cost function represented by a Kullback-Leibler divergence between the probability distribution associated with a state $|\psi(\vec{\theta})\rangle$ and a model implied by training data.

The quantum evolution training system minimizes the value of the cost function to determine updated values of the control parameters (step 304). In some implementations the quantum evolution training system minimizes the value of the cost function to determine updated values of the control parameters by adjusting the control parameters, e.g., adjusting physical control parameters. For example, the parameters that determine a pulse shape that may induce local fields on particular qubits may be adjusted by changing corresponding pixels on a voltage DAC. As another example, when the quantum hardware includes an ion trap the qubits may be controlled using lasers, and the parameters that determine a laser pulse shape or intensity may be adjusted. Other control parameters that may be adjusted include qubit frequencies or chip temperatures. The quantum evolution training system may minimize the value of the cost function to determine updated values of the control parameters by performing a gradient-free greedy minimization method, e.g., Powell's method or Nelder-Mead. For example, if the cost function is an expectation value of a quantum state and one or more system observables, the quantum evolution training system may perform a greedy minimization of the energy landscape in order to suggest a new setting of system parameters, e.g., hardware control parameters.

The quantum evolution training system iteratively performs steps 302 and 304 until it is determined that a completion event has occurred (step 306). In some implementations the completion event is that the determined value of the cost function that is based on the state and one or more of the system observables as described above with reference to step 302 converges.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computational systems" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible. The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons, or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators. Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for calibrating one or more quantum gates, the method comprising:
    for a classical processor in communication with quantum hardware, the quantum hardware comprising i) a quantum system comprising one or more multi-level quantum subsystems and ii) control devices that operate on the one or more multi-level quantum subsystems, wherein control parameters of the control devices comprise physical control parameters and form a variational ansatz:
        measuring, by the quantum hardware, an action of one or more quantum gates on the quantum system;
        comparing, by the classical processor, the measured action to a predefined target action of the one or more quantum gates;
        determining whether the measured action differs to the predefined target action; and
        in response to determining that the measured action differs to the predefined target action, adjusting the control parameters of the control devices to iteratively calibrate, within the variational ansatz, the action of the one or more quantum gates on the quantum system.

2. The method of claim 1, wherein iteratively calibrating the action of the one or more quantum gates on the quantum system comprises iteratively training changes from an initial quantum state to achieve a quantum state evolution that represents the predefined target action of the one or more quantum gates.

3. The method of claim 2, wherein the completion event is that the determined value of the cost function converges.

4. The method of claim 1, wherein iteratively calibrating the action of the one or more quantum gates on the quantum system comprises iteratively training, until the occurrence of a completion event, evolutions of an initial quantum state and subsequent quantum states to realize the predefined target action one or more quantum gates.

5. The method of claim 4, wherein the evolutions are analog evolutions.

6. The method of claim 1, wherein the iterative calibrating comprises, for each iteration:

determining a value of a cost function that is based on an initial ansatz wavefunction or a subsequent quantum state of the quantum system for the iteration and one or more of the quantum system observables;

minimizing the value of the cost function to determine updated values of the physical control parameters; and determining whether the completion event has occurred.

7. The method of claim 6, wherein minimizing the value of the cost function to determine updated values of the physical control parameters comprises adjusting the physical control parameters.

8. The method of claim 6, wherein the value of the cost function is an expectation value of the initial ansatz wavefunction or subsequent quantum state and one or more of the quantum system observables.

9. The method of claim 8, wherein determining an expectation value of the initial ansatz wavefunction or subsequent quantum state and one or more of the system observables comprises:

repeatedly preparing the initial ansatz wavefunction;

for each prepared ansatz wavefunction, measuring the one or more quantum system observables to determine a set of measurement results;

based on the set of measurement results, determining an expectation value of the subsequent quantum state of the quantum system and one or more of the system observables.

10. The method of claim 6, wherein determining an expectation value of the initial ansatz wavefunction or subsequent quantum state and one or more of the quantum system observables comprises determining an expectation value of a density operator and the one or more system observables.

11. An apparatus comprising:

quantum hardware comprising:

a quantum system comprising one or more multi-level quantum subsystems; and one or more control devices that operate on the multi-level quantum subsystems, wherein one or more control parameters of the one or more control devices i) comprise physical control parameters and ii) form a variational ansatz; and a classical processor configured to operate the quantum hardware;

wherein the apparatus is configured to perform operations comprising:

measuring an action of one or more quantum gates on the quantum system;

comparing the measured action to a predefined target action of the one or more quantum gates;

determining whether the measured action differs to the predefined target action; and in response to determining that the measured action differs to the predefined target action, adjusting the control parameters of the control devices to iteratively calibrate, within the variational ansatz, the action of the one or more quantum gates on the quantum system.

12. The apparatus of claim 11, wherein iteratively calibrating the action of the one or more quantum gates on the quantum system comprises iteratively training changes from an initial quantum state to achieve a quantum state evolution that represents the predefined target action of the one or more quantum gates.

13. The apparatus of claim 12, wherein the completion event is that the determined value of the cost function converges.

14. The apparatus of claim 11, wherein iteratively calibrating the action of the one or more quantum gates on the quantum system comprises iteratively training, until the occurrence of a completion event, evolutions of an initial quantum state and subsequent quantum states to realize the predefined target action one or more quantum gates.

15. The apparatus of claim 14, wherein the evolutions are analog evolutions.

16. The apparatus of claim 11, wherein the iterative calibrating comprises, for each iteration:

determining a value of a cost function that is based on an initial ansatz wavefunction or a subsequent quantum state of the quantum system for the iteration and one or more of the quantum system observables;

minimizing the value of the cost function to determine updated values of the physical control parameters; and determining whether the completion event has occurred.

17. The apparatus of claim 16, wherein minimizing the value of the cost function to determine updated values of the physical control parameters comprises adjusting the physical control parameters.

18. The apparatus of claim 16, wherein the value of the cost function is an expectation value of the initial ansatz wavefunction or subsequent quantum state and one or more of the quantum system observables.

19. The apparatus of claim 18, wherein determining an expectation value of the initial ansatz wavefunction or subsequent quantum state and one or more of the system observables comprises:

repeatedly preparing the initial ansatz wavefunction;

for each prepared ansatz wavefunction, measuring the one or more quantum system observables to determine a set of measurement results;

based on the set of measurement results, determining an expectation value of the subsequent quantum state of the quantum system and one or more of the system observables.

20. The apparatus of claim 16, wherein determining an expectation value of the initial ansatz wavefunction or subsequent quantum state and one or more of the quantum system observables comprises determining an expectation value of a density operator and the one or more system observables.

* * * * *